US006843775B2

(12) United States Patent
Hyun (10) Patent No.: US 6,843,775 B2
(45) Date of Patent: Jan. 18, 2005

(54) BLOOD DRAWING SYSTEM (75) Inventor: Dongchul D. Hyun, Brea, CA (US)

(73) Assignee: Smiths Medical ASD, Inc., Keene, NH (US)

( * ) Notice: Subject to any disclaimer, the term of this patent is extended or adjusted under 35 U.S.C. 154(b) by 326 days.

(21) Appl. No.: 09/867,148

(22) Filed: May 29, 2001

(65) Prior Publication Data

US 2002/0183651 A1 Dec. 5, 2002

(51) Int. Cl.$^7$ ................................. A61B 5/00
(52) U.S. Cl. ............... 600/573; 604/198; 604/5.03
(58) Field of Search ................. 604/6.15, 507, 604/198, 5.03; 600/573, 579, 580

(56) References Cited

U.S. PATENT DOCUMENTS

| 4,103,685 A | * | 8/1978 | Lupien et al. ............. 604/5.03 |
| 4,200,096 A | | 4/1980 | Charvin |
| 4,299,238 A | | 11/1981 | Baidwan et al. |
| 4,448,206 A | | 5/1984 | Martell |
| 4,572,210 A | | 2/1986 | McKinnon |
| 4,632,672 A | | 12/1986 | Kvitrud |
| 4,660,569 A | | 4/1987 | Etherington |
| 4,703,763 A | | 11/1987 | McAlister et al. |
| 4,935,009 A | * | 6/1990 | Caldwell et al. ............ 604/507 |
| 5,236,420 A | | 8/1993 | Pfleger |
| 5,238,003 A | | 8/1993 | Baidwan et al. |
| 5,377,689 A | | 1/1995 | Mercereau |
| 5,395,347 A | * | 3/1995 | Blecher et al. ............. 604/198 |

* cited by examiner

Primary Examiner—Thor Campbell
(74) Attorney, Agent, or Firm—Louis Woo (57) ABSTRACT A blood drawing system including a closeable first conduit through which drawn blood can flow; a first pressurizeable collection vessel for receiving blood therein; a hollow-shaft member; a second conduit leading from the first conduit to the first collection vessel; and a third conduit leading from the first conduit to the hollow shaft member connectable to a negative-pressure second collection vessel. Closing the first conduit allows blood transfer from the first vessel into the second vessel without exposure to or inclusion of any external devices to accomplish such transfer. Also included is an intravenous system with a conduit through which medicament liquid can be delivered and from which medicament liquid-free blood can be withdrawn. A first pressurizeable vessel first removes and conserves for reintroduction residual medicament liquid from the conduit, while thereafter a second negative-pressure vessel draws subsequent medicament liquid-free blood from the conduit.

30 Claims, 4 Drawing Sheets

BLOOD DRAWING SYSTEM

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention relates in general to blood drawing systems, and in particular to a blood drawing system which, in one embodiment, permits negative pressure control within a vessel to which blood is drawn for preventing vessel collapse because of excess pressure, and, in a second embodiment, for removing and conserving for re-introduction medicament liquid fed through an intravenous conduit prior to blood withdrawal through the intravenous conduit to a negative-pressure collection vessel.

Employment of negative-pressure vessels for collecting blood samples from arterial or venous blood vessels of living beings is a common practice in medical treatments where subsequent laboratory analysis of the blood samples so collected helps in diagnosing and treating illnesses. In those who are relatively healthy, the use of standard negative-pressure collection vessels, as exemplified by VACUTAINER brand tubes manufactured by Becton Dickinson, provide excellent withdrawal properties without causing vessel collapse. However, in patients whose vascular system is fragile, the negative pressure within a vacuum tube can be excessive, and such excessive negative pressure can cause vessel collapse as suction from the vacuum tube attempts to extract a blood sample.

At the present time, phlebotomists overcome this problem by drawing the blood sample into a standard syringe where negative pressure application can be controlled by the speed at which the plunger of the syringe is withdrawn. In this manner blood can be withdrawn slowly and without vessel collapse. However, the blood so drawn into a syringe then must be transferred to a vacuum tube because of required anticoagulant and/or other blood-preservation additives present in the vacuum tube. Such transfer can only be accomplished by attaching a standard hollow needle to the syringe, piercing the stopper can of the vacuum tube, and expelling the syringe content into the vacuum tube. As is recognized to those with ordinary skill in the art, the above-described attachment of the needle to the syringe is potentially a very dangerous event because an easily-occurring finger-stick of the technician performing the task can mean the transfer of patient blood to the technician along with blood-borne disease. Therefore, a primary object of the present invention is to permit blood transfer from a drawing syringe to a negative-pressure collection vessel through a closed network not requiring attachment of a needle to the syringe.

A second situation where blood-sample withdrawal is required is in connection with a typical intravenous drip line having a port to which a negative-pressure collection vessel (e.g. a vacuum tube) can be connected for easy blood withdrawal through the line. As is evident, however, if the line is not first cleared of drip-liquid, any blood sample will have a high amount of such medicament liquid and therefore will not provide a true blood-only sample. This problem presently is addressed by turning off the drip from its source and thereafter withdrawing and discarding all fluid from the drip line prior to opening the port to the vacuum tube. As is evident, this approach not only decreases (and wastes) the intended drip-liquid amount for the patient, but also causes loss of at least a small amount of blood from the patient as the drip line is filled with only blood for vacuum tube collection. One or both of these disadvantages can be harmful to a patient. In particular, if the amount of drip-liquid to be delivered to a patient is critical, such amount is automatically compromised with drip-liquid loss. Second, if the patient is a neonatal child with a corresponding very low volume of blood, even a small blood loss which occurs during each drip line clearance can create a dangerous health hazard. Consequently, a second object of the present invention is to provide a closed drip-line system in which medicament liquid cleared from the drip line prior to blood withdrawal into the vacuum tube is collected for reintroduction after the blood sample has been drawn. In this manner, both drip-liquid and blood volume are conserved for the patient.

These and other objects of the present invention will become apparent throughout the description thereof which now follows.

BRIEF SUMMARY OF THE INVENTION

The present invention first provides a blood drawing system for drawing blood from a blood vessel of a living being. This system comprises a selectively-closeable first conduit through which blood drawn from a blood vessel can flow; a first collection vessel for receiving blood and having an exteriorly-operable pressure controller for application of negative or positive pressure therein; a hollow-shaft member; a second conduit having a first end in fluid communication with the first conduit and a second end in fluid communication with the first collection vessel; and a third conduit having a first end in communication with the first conduit and a second end in communication with the hollow shaft member. In operation, a negative pressure second collection vessel is connected in fluid communication with the hollow shaft member. Thereafter, the closing of the first conduit allows medicament liquid transfer from the first collection vessel through the hollow shaft member and into the second collection vessel upon positive pressure application with the pressure controller within the first collection vessel without exposure to or inclusion of any external devices to accomplish such transfer. In a preferred embodiment, the first collection vessel is a standard syringe with a plunger therein, the hollow shaft member is a needle, and the second collection vessel is a standard vacuum tube with a needle-penetrable stopper which is so penetrated by the hollow shaft member.

The present invention further provides an intravenous system for delivering a medicament liquid to a blood vessel and for collecting blood from the blood vessel through the system, yet substantially free of the medicament liquid. The system comprises a vascular first conduit having a first end thereof for liquid communication with a storage container for storing the medicament liquid and a second end thereof for liquid communication with the blood vessel; a first collection vessel for receiving blood and having an exteriorly-operable pressure controller for application of negative or positive pressure within the first collection vessel; a hollow shaft member; a selectively closeable second conduit having a first end in fluid communication with the first conduit and a second end in fluid communication with the first collection vessel; and a selectively closeable third conduit having a first end in fluid communication with the first conduit and a second end in fluid communication with the hollow shaft member. In operation, a negative pressure second collection vessel is connected in fluid communication with the hollow shaft member. Thereafter, closing the third conduit, opening the second conduit, and applying negative pressure to the first collection vessel collects in the first collection vessel at least substantially all medicament liquid present within the first conduit, and thereafter closing the second conduit and opening the third conduit directs substantially medicament liquid-free blood resultantly present within the first conduit through the third conduit and the hollow shaft member into the second collection vessel.

As is thus apparent, the present invention accomplishes blood transfer from a drawing syringe to a negative-pressure collection vessel through a closed network not requiring attachment of a needle to the syringe, and additionally accomplishes a closed drip-line system in which medicament liquid cleared from the drip line prior to blood withdrawal is conservedly collected for reintroduction after the blood sample has been drawn.

BRIEF DESCRIPTION OF THE DRAWINGS

An illustrative and presently preferred embodiment of the invention is shown in the accompanying drawings in which.

DETAILED DESCRIPTION OF THE INVENTION

Figure 1:
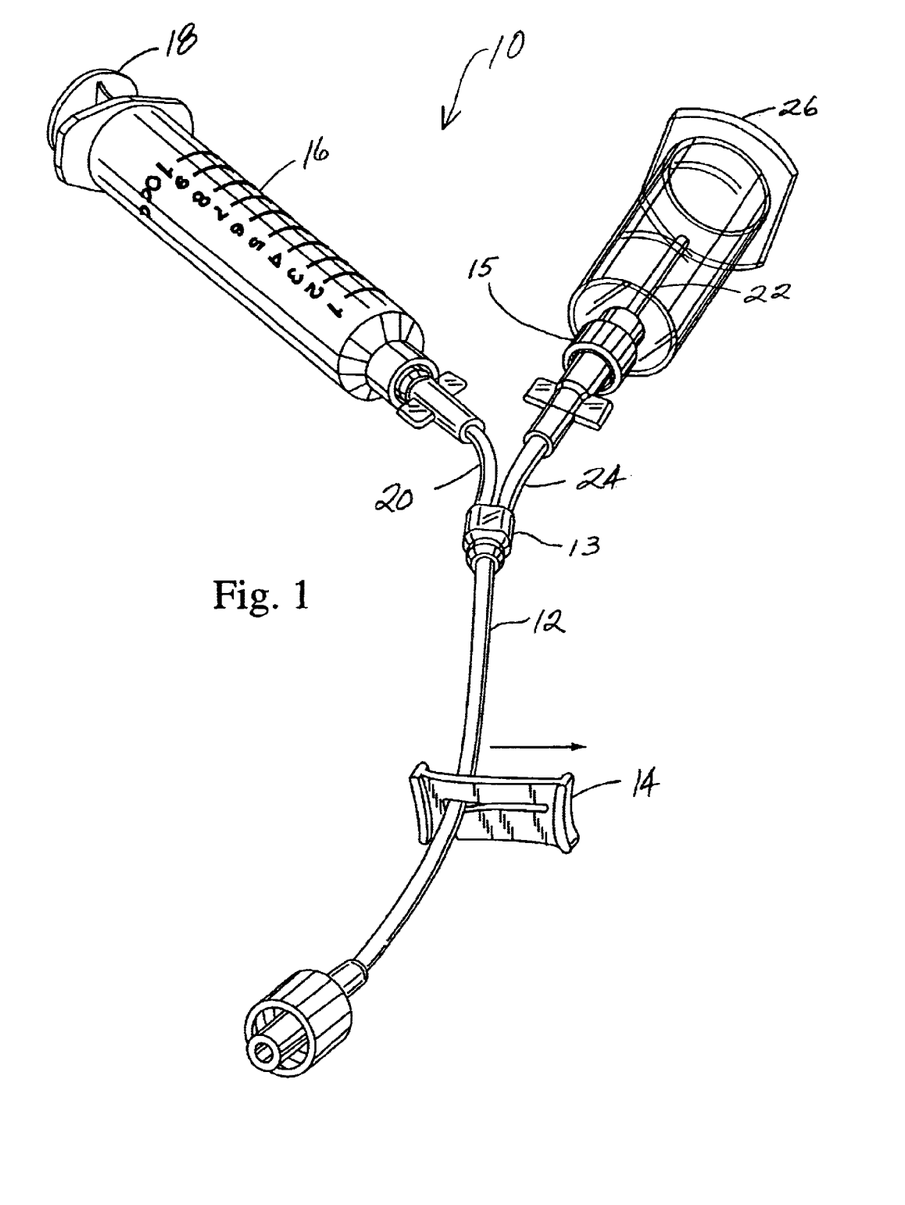
FIG. 1 is a perspective view of a blood drawing system showing an open clamp on a blood-transfer conduit.
Figure 2:
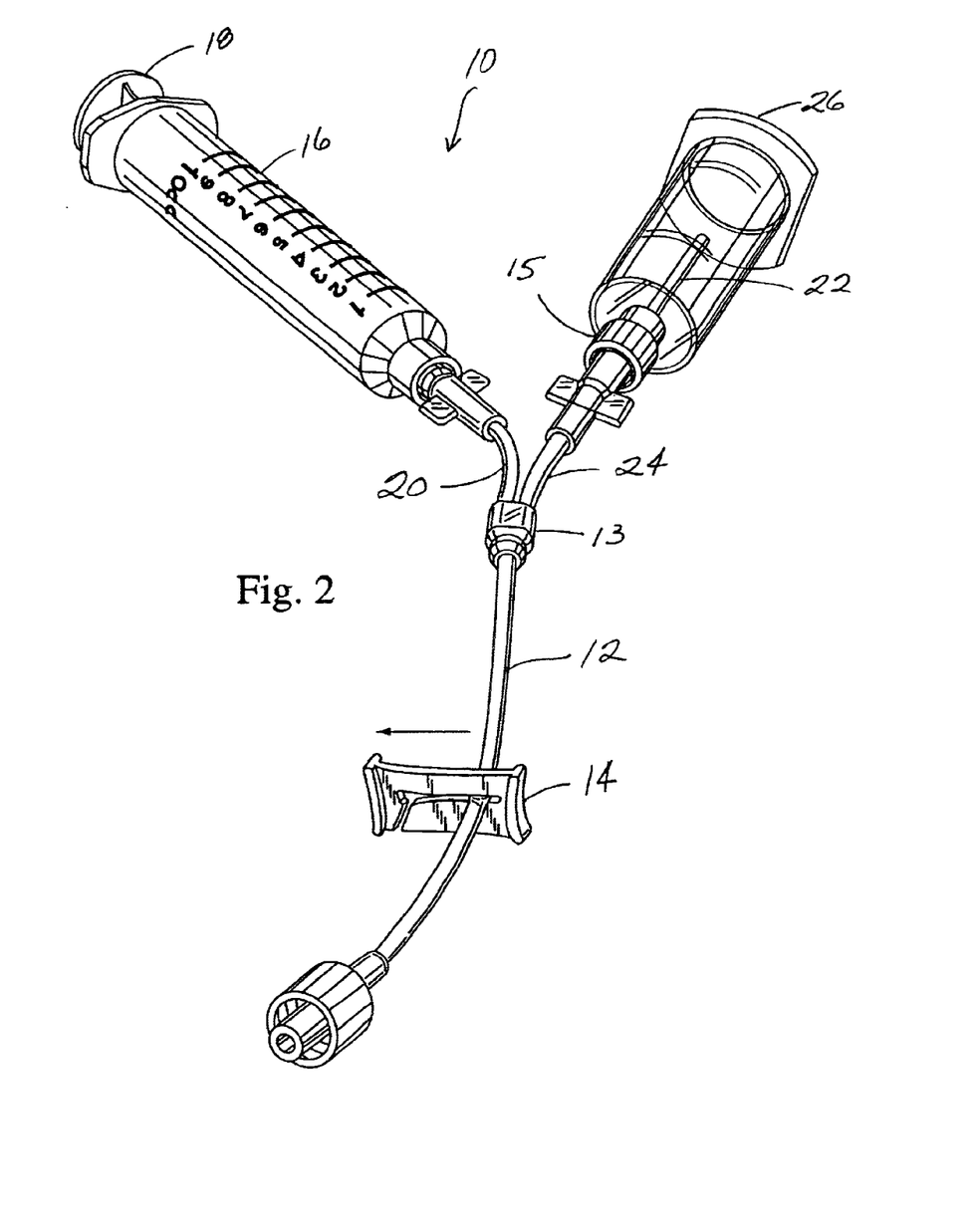
FIG. 2 is a perspective view of the blood drawing system of FIG. 1 showing a closed clamp.

Referring first to FIGS. 1 and 2, a blooddrawing system 10 is shown. The system 10 includes a first conduit 12 through which blood from a blood vessel (not shown) of a patient can flow upon standard needle entry thereto. The needle may be connected to conduit 12 by way of a luer connector 11. The first conduit 12 is provided with a closure member here non-limitedly shown as a sliding clamp 14, with FIG. 1 showing the clamp 14 in an open position and FIG. 2 showing it in a closed position. A standard syringe 16 functions as a first collection vessel for receiving blood, and has a standard exteriorly-operable plunger 18 for controllably applying negative or positive pressure within the syringe 16. A second conduit 20 has a first end thereof in fluid communication with the first conduit 12 via a conduit connector 13 and a second end thereof in fluid communication with the syringe 16. The system 10 includes a hollow-shaft member here non-limitedly exemplified as a hollow needle 22 and a third conduit 24 having a first end thereof in fluid communication with the first conduit 12 by way of conduit connector 13. Fluid connector 13 provides a junction whereby respective fluid paths may be provided between the patient and syringe 16, the patient and needle 22, and syringe 16 and needle 22. A second end of third conduit 24 is fitted with a luer connector 15, which when mated with needle 22, establishes in fluid communication with the needle 22. Preferred operation includes a fluid communication of the needle 22 with a standard vacuum tube such as a VACUTAINER brand tube as earlier identified (not shown) through a needle-penetrable stopper, with the tube conventionally retained in a tube holder 26 as known in the art. As is apparent, closing the first conduit 12 allows medicament liquid transfer from the syringe 16 through the needle 22 upon positive pressure application with the plunger 18.

In operation, the first conduit 12 is connected to a catheter (not shown) leading from a blood vessel of the patient such that blood can flow into the first conduit 12. The clamp 14 is open (FIG. 1) and an operator withdraws the plunger 18 of the syringe 16 to create negative pressure and cause blood entry into the syringe 16. After such blood-sample collection is complete, plunger activity is ceased and the clamp 14 is closed (FIG. 2). A vacuum tube is fixed in fluid connection with the needle 22 and the blood from the syringe 16 is moved therefrom by positive pressure created by inward operator movement of the plunger 18. The blood from the syringe 16 first travels through the second conduit 20 into the first conduit 12 to the site of the clamp 14, and then returns into the third conduit 24 for continued travel through the hollow needle 22 and into the vacuum tube. Typically, the vacuum tube will have an anticoagulant therein which preserves the blood sample in analytical condition for a sufficient amount of time such that laboratory procedures can be completed. To this end, the vacuum tube is withdrawn from the holder 26 for such laboratory delivery.

Figure 3:
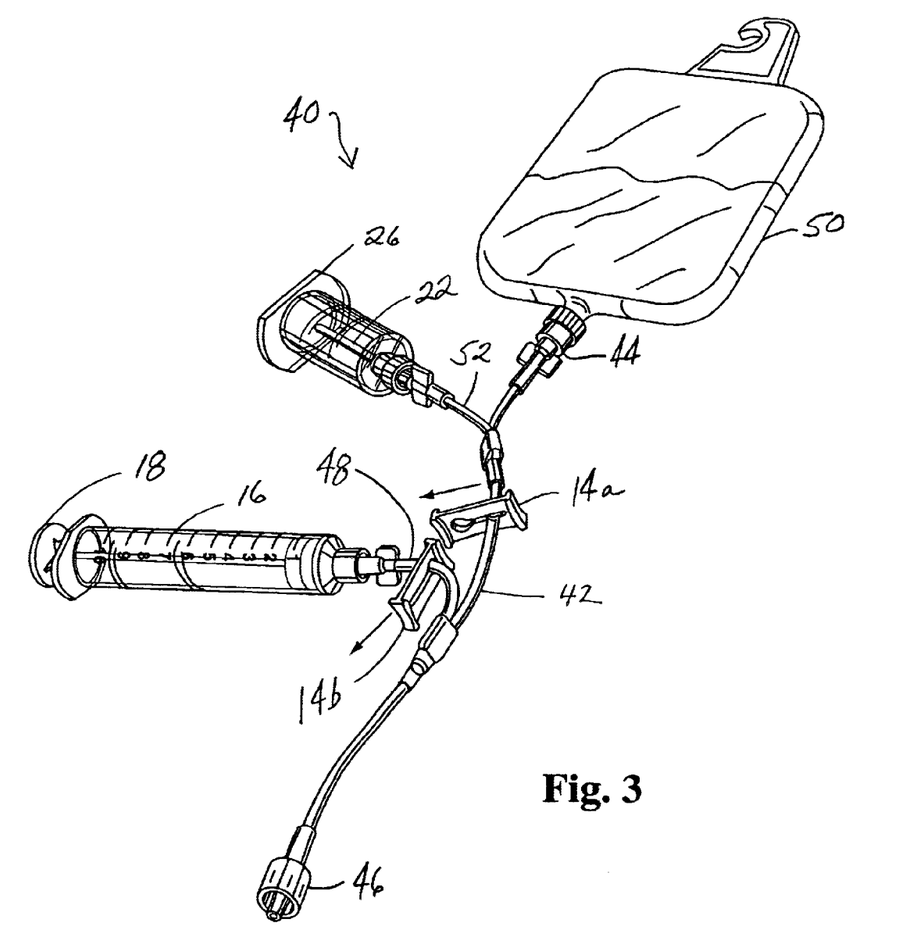
FIG. 3 is a perspective view of an intravenous system for delivering a medicament liquid to a blood vessel and for collecting blood through the system, showing one clamp thereof open and one clamp thereof closed.
Figure 4:
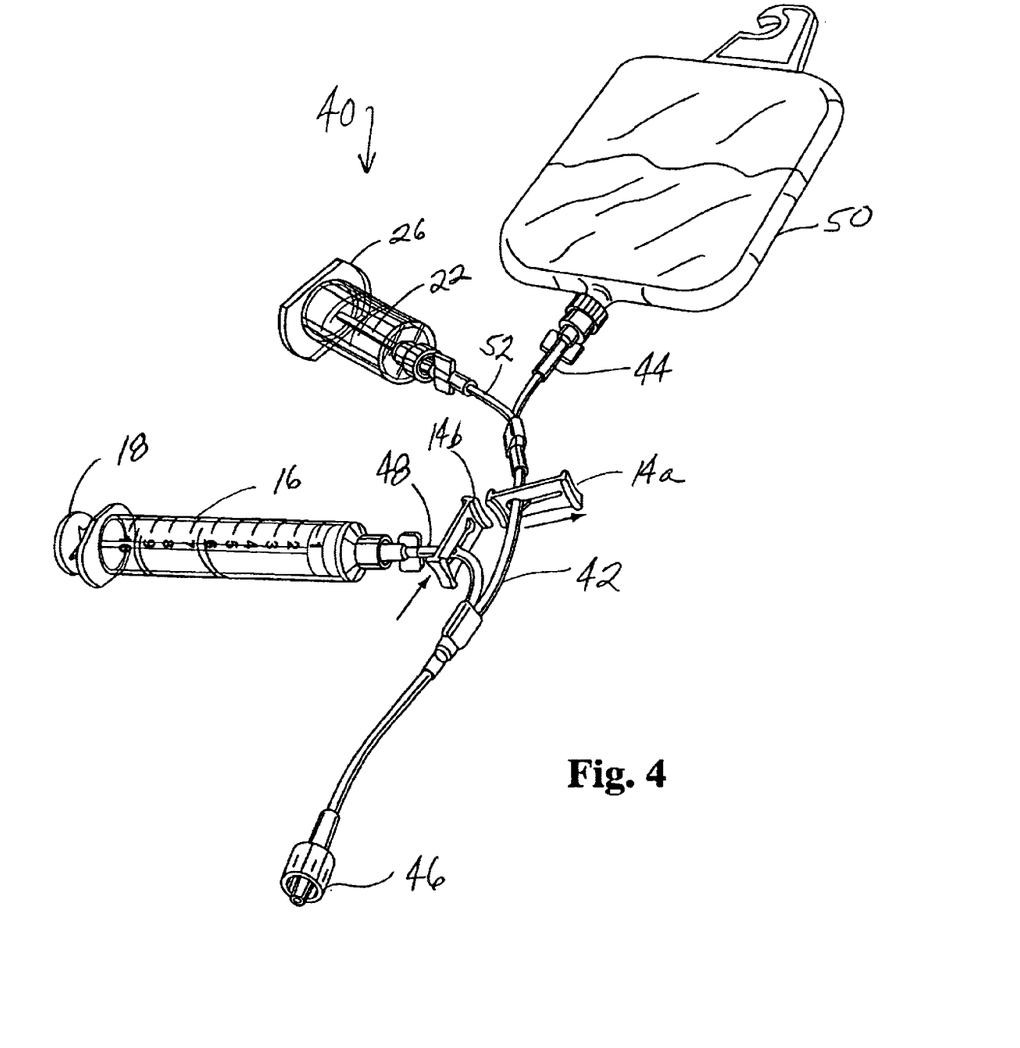
FIG. 4 is a perspective view of the intravenous system of FIG. 3 with clamp positions reversed.

Referring now to FIGS. 3 and 4, an intravenous system 40 for delivering a medicament liquid to a blood vessel (not shown) and for collecting blood from the blood vessel through the same system 40 is illustrated. In particular, the system includes a connecting vascular first conduit 42 having a first end 44 for receiving medicament liquid as from a standard IV drip bag 50 (or fluid store) and a second end 46 thereof for fluid communication via a standard catheter (not shown) or the like with the blood vessel. The first conduit 42 is provided with a closure member here nonlimitedly shown as a sliding clamp 14a, with FIG. 3 showing the clamp 14a in a closed position and FIG. 4 showing it in an open position. A standard syringe 16 functions as a first collection vessel, and has a standard exteriorly-operable plunger 18 for controllably applying negative or positive pressure within the syringe 16. A second conduit 48 has a first end thereof in fluid communication with the first conduit 42 and a second end thereof in fluid communication with the syringe 16, and is provided with a sliding clamp 14b shown in an open position in FIG. 3 and a closed position in FIG. 4. The system 40 includes a hollow-shaft member here non-limitedly exemplified as a hollow needle 22 and a third conduit 52 having a first end thereof in fluid communication with the first conduit 42 and a second end thereof in fluid communication with the needle 22. Preferred operation includes a fluid communication of the needle 22 with a standard vacuum tube such as a VACUTAINER brand tube as earlier identified (not shown) through a needle-penetrable stopper, with the tube conventionally retained in a tube holder 26 as known in the art. As is apparent, closing the first conduit 42 with the clamp 14a prohibits fluid movement upstream from the second conduit 48, while closure of the second conduit 48 with the clamp 14b prohibits fluid movement through the second conduit 48.

In operation during traditional medicament liquid delivery from the drip bag 50 to a blood vessel, most commonly a vein, of a patient, the first conduit 42 is connected at its first end to the drip bag 50 and at its second end to a catheter or the like (not shown) leading to the blood vessel. The clamp 14a is in the open position while the clamp 14b is in the closed position, thereby permitting medicament liquid flow into the blood vessel. When a blood sample is needed during such medicament liquid delivery and is to be withdrawn through the first conduit 42, an operator first closes the clamp 14a to thereby stop medicament liquid flow from the drip bag 50. Since the first conduit 42 still contains medicament liquid downstream from the clamp 14a and therefore can not yield a generally medicament liquid-free blood sample if drawn through the first conduit 42, it is necessary to remove such medicament liquid prior to blood-sample withdrawal. Such medicament liquid removal is accomplished by opening the clamp 14b of the second conduit 48 and withdrawing the plunger 18 of the syringe 16 to create negative pressure within the syringe 16 and draw the medicament liquid still in the first conduit 42. Such medicament liquid withdrawal is continued until blood becomes present within the syringe, at which time the clamp 14b is closed. A vacuum tube is fixed in fluid connection with the needle 22 and the clamp 14a of the first conduit is then opened to permit the substantially medicament liquid-free blood now present in the first conduit 42 to travel through the hollow needle 22 into the vacuum tube. Once this blood sample is collected in the vacuum tube, the vacuum tube is withdrawn from the holder 26, the clamp 14a is closed, the clamp 14b is opened, and the medicament liquid and blood present in the syringe 16 is forced by inward movement of the plunger 18 back through the second conduit 48 into the first conduit 42 for return to the patient while the clamp 14a is again opened to permit medicament liquid flow from the drip bag 50 through the first conduit 42 and into the blood vessel. In this manner, a closed drip-line system is provided in which medicament liquid cleared from the first conduit 42 prior to blood withdrawal is conservedly collected and thereafter returned to the patient after the blood sample has been drawn.

While illustrative and presently preferred embodiments of the invention have been described in detail herein, it is to be understood that the inventive concepts may be otherwise variously embodied and employed and that the appended claims are intended to be construed to include such variations except insofar as limited by prior art.

What is claimed is:

1. A blood drawing system for drawing blood from a blood vessel of a living being, the system comprising:
   a) a first conduit through which blood drawn from a blood vessel can flow, said first conduit having a closure member for selectively closing the first conduit at a closure site thereof;
   b) a first collection vessel for receiving blood and having an exteriorly-operable pressure controller for application of negative or positive pressure within said first collection vessel;
   c) a hollow-shaft member;
   d) a second conduit having a first end in fluid communication with the first conduit and a second end in fluid communication with the first collection vessel; and
   e) a third conduit having a first end in communication with the first conduit and a second end in communication with the hollow shaft member;
   wherein when said first conduit is closed by said closure member and positive pressure is applied within the first collection vessel by the pressure controller, liquid is transferred from the first collection vessel through the hollow shaft member.

2. A blood drawing system as claimed in claim 1 wherein the closure member of the first conduit is a clamp.

3. A blood drawing system as claimed in claim 1 wherein the first collection vessel is a syringe.

4. A blood drawing system as claimed in claim 3 wherein the pressure controller is a plunger within said syringe.

5. A blood drawing system as claimed in claim 1 wherein the hollow shaft member is a needle.

6. A blood drawing system for drawing blood from a blood vessel of a living being, the system comprising:
   a) a first conduit through which blood drawn from a blood vessel can flow, said first conduit having a clamp provided thereto for selectively closing the first conduit;
   b) a syringe for receiving blood and having an exteriorly-operable plunger for application of negative or positive pressure within the syringe;
   c) a hollow needle;
   d) a second conduit having a first end in fluid communication with the first conduit and a second end in fluid communication with the syringe; and
   e) a third conduit having a first end in communication with the first conduit and a second end in communication with the hollow needle;
   wherein when said first conduit is closed and positive pressure is applied within the syringe by the plunger, liquid is transferred from the syringe through the hollow needle.

7. A method of drawing blood from a blood vessel of a living being, the method comprising:
   a) connecting a blood vessel conduit leading from the blood vessel to a blood drawing system, the system comprising:
      i) a first conduit through which blood from the blood vessel conduit can flow, said first conduit having a closure member for selectively closing the first conduit at a closure site thereof;
      ii) a first collection vessel for receiving blood and having an exteriorly-operable pressure controller for application of negative or positive pressure within said first collection vessel;
      iii) a hollow-shaft member;
      iv) a second conduit having a first end in fluid communication with the first conduit and a second end in fluid communication with the first collection vessel; and
      v) a third conduit having a first end in communication with the first conduit and a second end in communication with the hollow shaft member, whereby closing the first conduit allows liquid transfer from the first collection vessel through the hollow shaft member upon application of positive pressure within the first collection vessel by the pressure controller;
   b) connecting a second collection vessel having a negative pressure therein in fluid communication with the hollow shaft member;
   c) operating the pressure controller to effect a negative pressure within the first collection vessel for drawing blood from the first conduit through the second conduit into the first collection vessel;
   d) closing the first conduit at the closure site thereof;
   e) operating the pressure controller to effect a positive pressure within the first collection vessel for forcing blood from the first collection vessel through the second conduit into the first conduit to the closure site thereof and thereafter into the third conduit and delivery into the second collection vessel; and f) removing the second collection vessel from the system.

8. A method of drawing blood as claimed in claim 7 wherein in the blood drawing system the closure member of the first conduit is a clamp.

9. A method of drawing blood as claimed in claim 7 wherein in the blood drawing system the first collection vessel is a syringe.

10. A method of drawing blood as claimed in claim 9 wherein in the blood drawing system the pressure controller is a plunger within said syringe.

11. A method of drawing blood as claimed in claim 7 wherein the second collection vessel is a vacuum tube with a needle-penetrable stopper closing a single entrance to said vacuum tube.

12. A method of drawing blood from a blood vessel of a living being, the method comprising:
- a) connecting a blood vessel conduit leading from the blood vessel to a blood drawing system, the system comprising:
  - i) a first conduit through which blood from the blood vessel conduit can flow, said first conduit having a clamp for selectively closing the first conduit at a closure site thereof;
  - ii) a syringe for receiving blood and having an exteriorly-operable plunger for application of negative or positive pressure within the syringe;
  - iii) a hollow needle;
  - iv) a second conduit having a first end in fluid communication with the first conduit and a second end in fluid communication with the syringe; and
  - v) a third conduit having a first end in communication with the first conduit and a second end in communication with the needle, whereby closing the first conduit allows liquid transfer from the syringe through the needle upon application of positive pressure within the syringe by the plunger;
- b) connecting a vacuum tube in fluid communication with the needle;
- c) operating the plunger to effect a negative pressure within the syringe for drawing blood from the first conduit through the second conduit into the syringe;
- d) closing the first conduit at the closure site thereof;
- e) operating the plunger to effect a positive pressure within the syringe for forcing blood from the syringe through the second conduit into the first conduit to the closure site thereof and thereafter into the third conduit and delivery into the vacuum tube; and
- f) removing the vacuum tube from the system.

13. An intravenous system for delivering a medicament liquid to a blood vessel and for collecting blood from the blood vessel through the system and substantially free of said medicament liquid, the system comprising:
- a) a vascular first conduit having a first end thereof for liquid communication with a storage container storing the medicament liquid and a second end thereof for liquid communication with the blood vessel;
- b) a first collection vessel for receiving blood and having an exteriorly-operable pressure controller for application of negative or positive pressure within said first collection vessel;
- c) a hollow shaft member;
- d) a second conduit having a first end in fluid communication with the first conduit and a second end in fluid communication with the first collection vessel, said second conduit having a closure member for selectively closing the second conduit; and
- e) a third conduit having a first end in fluid communication with the first conduit and a second end in fluid communication with the hollow shaft member, said third conduit having a closure member for selectively closing the third conduit, whereby closing the third conduit, opening the second conduit, and applying negative pressure to the first collection vessel collects in said first collection vessel at least substantially all medicament liquid within the first conduit, and thereafter closing the second conduit and opening the third conduit directs substantially medicament liquid-free blood within the first conduit as present from the blood vessel.

14. An intravenous system for delivering a medicament liquid to a blood vessel as claimed in claim 13 wherein each closure member is a clamp.

15. An intravenous system for delivering a medicament liquid to a blood vessel as claimed in claim 13 wherein the first collection vessel is a syringe.

16. An intravenous system for delivering a medicament liquid to a blood vessel as claimed in claim 15 wherein the pressure controller is a plunger within said syringe.

17. An intravenous system for delivering a medicament liquid to a blood vessel as claimed in claim 15 wherein the hollow shaft member is a needle.

18. A method of drawing blood through an intravenous medicament liquid-delivery blood vessel conduit from a blood vessel of a living being, the method comprising:
- a) connecting the blood vessel conduit leading from the blood vessel to a blood drawing system, the system comprising:
  - i) a vascular first conduit having a first end thereof for liquid communication with a storage container for storing the medicament liquid and a second end thereof for liquid communication with the blood vessel;
  - ii) a first collection vessel for receiving at least medicament liquid and having an exteriorly-operable pressure controller for application of negative or positive pressure within said first collection vessel;
  - iii) a hollow shaft member;
  - iv) a second conduit having a first end in fluid communication with the first conduit and a second end in fluid communication with the first collection vessel, said second conduit having a closure member for selectively closing the second conduit; and
  - v) a third conduit having a first end in fluid communication with the first conduit and a second end in fluid communication with the hollow shaft member, said third conduit having a closure member for selectively closing the third conduit, whereby closing the third conduit, opening the second conduit, and applying negative pressure to the first collection vessel collects in said first collection vessel at least substantially all medicament liquid within the first conduit, and thereafter closing the second conduit and opening the third conduit directs substantially medicament liquid-free blood within the first conduit as present from the blood vessel;
- b) connecting a second collection vessel having a negative pressure therein in fluid communication with the hollow shaft member;
- c) closing the closure member of the third conduit, opening the closure member of the second conduit, and operating the pressure controller and creating a negative pressure within the first collection vessel for drawing at least medicament liquid from the first conduit through the second conduit into the first collection vessel;

d) closing the closure member of the second conduit, opening the closure member of the third conduit, and collecting substantially medicament liquid-free blood from within the first conduit as present from the blood vessel into the second collection vessel; and e) closing the closure member of the third conduit and removing the second collection vessel from the system.

19. A method of drawing blood through an intravenous medicament liquid-delivery blood vessel conduit as claimed in claim 18 wherein in the blood drawing system each closure member is a clamp.

20. A method of drawing blood through an intravenous medicament liquid-delivery blood vessel conduit as claimed in claim 18 wherein in the blood drawing system the first collection vessel is a syringe.

21. A method of drawing blood through an intravenous medicament liquid-delivery blood vessel conduit as claimed in claim 20 wherein in the blood drawing system pressure controller is a plunger within said syringe.

22. A method of drawing blood through an intravenous medicament liquid-delivery blood vessel conduit as claimed in claim 18 wherein the second collection vessel is a vacuum tube with a needle-penetrable stopper closing a single entrance to said vacuum tube.

23. A method of drawing blood through an intravenous medicament liquid-delivery blood vessel conduit from a blood vessel of a living being, the method comprising:

a) connecting the blood vessel conduit leading from the blood vessel to a blood drawing system, the system comprising:
 i) a vascular first conduit having a first end thereof for liquid communication with a storage container for storing the medicament liquid and a second end thereof for liquid communication with the blood vessel;
 ii) a syringe for receiving at least medicament liquid and having an exteriorly operable plunger for application of negative or positive pressure within said first collection vessel;
 iii) a hollow needle;
 iv) a second conduit having a first end in fluid communication with the first conduit and a second end in fluid communication with the syringe, said second conduit having a clamp for selectively closing the second conduit; and
 v) a third conduit having a first end in fluid communication with the first conduit and a second end in fluid communication with the hollow needle, said third conduit having a closure member for selectively closing the third conduit, whereby closing the third conduit, opening the second conduit, and applying negative pressure to the syringe collects in said syringe at least substantially all medicament liquid within the first conduit, and thereafter closing the second conduit and opening the third conduit directs substantially medicament liquid-free blood within the first conduit as present from the blood vessel;

b) connecting a vacuum tube in fluid communication with the needle;

c) closing the closure member of the third conduit, opening the closure member of the second conduit, and operating the plunger and creating a negative pressure within the syringe for drawing at least medicament liquid from the first conduit through the second conduit into the syringe;

d) closing the closure member of the second conduit, opening the closure member of the third conduit, and collecting substantially medicament liquid-free blood from within the first conduit as present from the blood vessel into the vacuum tube; and e) closing the closure member of the third conduit and removing the vacuum tube from the system.

24. Apparatus comprising:

at least a first conduit for establishing a first fluid path between a blood vessel of a patient and a first fluid collection vessel whereinto a positive pressure or a negative pressure may be applied;

at least a second conduit for establishing a second fluid path between said first fluid collection vessel and a needle; and a closure member associated with said first conduit effective for selectively opening or closing said first fluid path;

wherein when said closure member is operated to open said first fluid path and a negative pressure is applied within said first fluid collection vessel, fluid from the patient flows through said first fluid path and is collected in said first fluid collection vessel; and wherein when said closure member is operated to close said first fluid path and a positive pressure is applied within said first fluid collection vessel, said second fluid path is operable to allow fluid stored in said first fluid collection vessel to flow through said second fluid path to said needle and be collected in a second fluid collection vessel mated to said needle.

25. Apparatus of claim 24, wherein said first fluid collection vessel is a syringe and said fluid collection vessel is a vacuum tube, said needle being a part of a vacuum tube holder to which said vacuum tube is inserted.

26. A fluid routing apparatus, comprising:

a first conduit having a first end connectable to a patient and a second end connected to a conduit connector;

second conduit having a first end connectable to a syringe and a second end connected to said conduit connector;

a third conduit having a needle at its first end and a second end connected to said conduit connector;

a closure member associated with said first conduit effective for selectively opening or closing said first fluid path;

wherein when said closure member is operated to open said first conduit, at least a first fluid path is established between said first conduit and said second conduit for flow of fluid between the patient and the syringe; and wherein when said closure member is operated to close said first conduit, at least a second fluid path is established between said syringe and said needle.

27. Apparatus of claim 26, wherein said first end of said first conduit is mated to a luer connector to which a needle may be connected for insertion to a vein of the patient; and wherein the first end of said third conduit has a luer connector to which a vacuum tube holder is mated.

28. Apparatus comprising:

at least a first conduit for establishing a first fluid path between a patient and a syringe whereinto a positive pressure or a negative pressure may be applied;

at least a second conduit for establishing a second fluid path between said syringe and a needle;

at least a third conduit for establishing a third fluid path between the patient and a fluid store;

a first closure member associated with said first fluid path effective for selectively opening or closing said first fluid path; and a second closure member associated with at least said second fluid path for selectively opening or closing said second fluid path;

wherein when said first closure member is operated to open said first fluid path and said second closure member is operated to close said second fluid path, and a negative pressure is applied within said syringe, fluid in said first fluid path is collected in said syringe.

29. Apparatus of claim 28, wherein when said first closure member is operated to close said first fluid path and said second closure member is operated to open said second fluid path, said second fluid path is operable to allow either the fluid stored in said fluid store to flow to the patient or fluid from the patient to be drawn to said needle if a vacuum tube is mated to said needle and fluid is not being provided to the patient from said fluid store; and wherein the fluid stored in said syringe may be injected to said first fluid path when said first closure member is operated to open said first fluid path and said second closure member is operated to close said second fluid path, and a positive pressure is applied within said syringe.

30. A fluid routing apparatus, comprising:

a first conduit having a first end connectable to a patient and a second end connected to a first conduit connector;

a second conduit having a first end connectable to a syringe and a second end connected to said first conduit connector, said first and second conduits effective to establish a first fluid path;

a third conduit having a first end connected to said first conduit connector and a second end connected to a second conduit connector;

a fourth conduit having a first end connected to a needle and a second end connected to said second conduit connector, said first, third and fourth conduits effective to establish a second fluid path;

a fifth conduit having a first end connectable to a fluid store and a second end connected to said second conduit connector, said first, third and fifth conduits effective to establish a third fluid path;

a first closure member associated with said first fluid path effective for selectively opening or closing said first fluid path; and a second closure member associated with said second fluid path effective for selectively opening or closing said second and third fluid paths;

wherein when said first closure member is operated to open said first fluid path and said second closure member is operated to close said second and third fluid paths, fluid communication is established between the patient and the syringe; and wherein when said closure member is operated to close said first fluid path and said second closure member is operated to open said second and third fluid paths, fluid communication is established between the patient and at least one of said needle and fluid store.

* * * * *